United States Patent
Green et al.

(10) Patent No.: US 6,709,380 B2
(45) Date of Patent: Mar. 23, 2004

(54) BRACHYTHERAPY NEEDLE WITH IMPEDANCE MEASUREMENT APPARATUS AND METHODS OF USE

(75) Inventors: Thomas C. Green, Seattle, WA (US); Michael Hogendijk, Palo Alto, CA (US); Keith Seiler, Issaquah, WA (US); Larry DeSoto, Seattle, WA (US); Edo Ziring, Mercer Island, WA (US)

(73) Assignee: Neoseed Technology LLC, San Francisco, CA (US)

( * ) Notice: Subject to any disclaimer, the term of this patent is extended or adjusted under 35 U.S.C. 154(b) by 0 days.

(21) Appl. No.: 09/873,666

(22) Filed: May 31, 2001

(65) Prior Publication Data

US 2002/0183582 A1 Dec. 5, 2002

(51) Int. Cl.[7] .............................. A61B 5/05; A61N 5/00
(52) U.S. Cl. ........................................... 600/3; 600/547
(58) Field of Search ............................... 600/3, 7, 547; 606/41, 46; 604/272, 264

(56) References Cited

U.S. PATENT DOCUMENTS

| | | | |
|---|---|---|---|
| 2,763,935 A | * | 9/1956 | Whaley et al. ............. 604/264 |
| 4,224,949 A | * | 9/1980 | Scott et al. ................. 600/373 |
| 4,291,708 A | | 9/1981 | Frei et al. |
| 4,458,694 A | | 7/1984 | Sollish et al. |
| 4,679,561 A | | 7/1987 | Doss |
| 5,143,079 A | | 9/1992 | Frei et al. |
| 5,271,413 A | * | 12/1993 | Dalamagas et al. ......... 128/734 |
| 5,335,668 A | * | 8/1994 | Nardella ...................... 128/734 |
| 5,415,177 A | * | 5/1995 | Zadini et al. ............... 128/772 |
| 5,423,796 A | * | 6/1995 | Shikhman et al. ............. 606/1 |
| 5,429,636 A | * | 7/1995 | Shikhman et al. ............ 606/41 |
| 5,683,384 A | | 11/1997 | Gough et al. |
| 5,715,825 A | | 2/1998 | Crowley |
| 5,800,484 A | | 9/1998 | Gough et al. |
| 5,916,153 A | | 6/1999 | Rhea, Jr. |
| 5,928,130 A | | 7/1999 | Schmidt |
| 5,928,159 A | | 7/1999 | Eggers et al. |
| 5,938,583 A | * | 8/1999 | Grimm .......................... 600/7 |
| 5,947,964 A | | 9/1999 | Eggers et al. |
| 6,080,149 A | | 6/2000 | Huang et al. |
| 6,106,524 A | | 8/2000 | Eggers et al. |
| 6,337,994 B1 | * | 1/2002 | Stoianovici et al. ........ 600/547 |
| 6,391,005 B1 | * | 5/2002 | Lum et al. .................. 604/117 |
| 2001/0049510 A1 | * | 12/2001 | Burr et al. .................. 604/272 |

FOREIGN PATENT DOCUMENTS

| | | | |
|---|---|---|---|
| DE | 4420232 | * | 12/1995 |
| FR | 2590476 | * | 5/1987 |

OTHER PUBLICATIONS

Scuenn–Tsong Young et al, "An Instrument Using Variation of Resistance to Aid in Needle Tip Insertion in Epidural Block in Monkeys," Medical Instrumentation (Oct. 1987), vol. 21, No. 5, p. 266–8.*

Lee, B.R., "Bioimpedance: Novel Use of a Minimally Invasive Technique for Cancer localization in the Intact Prostate," Prostate, 39(3), pp. 213–218, May 15, 1999.*

Morimoto, T., "Measurement of the Electrical Bio–Impedance of Breast Tumors," *Eur. Surg. Res. 22:* 86–92 (1990).

* cited by examiner

Primary Examiner—John A. Jeffery
(74) Attorney, Agent, or Firm—Fish & Neave; Daniel M. Becker; Douglas A. Oguss

(57) ABSTRACT

Apparatus and methods for depositing radioactive seeds into a patient's prostate are provided that include impedance measuring circuitry for detecting whether the distal end of an elongated needle extends into a patient's bladder. The elongated needle includes two conductive traces and a lumen adapted to receive a column of radioactive seeds and spacers. The impedance measuring circuitry is coupled to the conductive traces of the elongated needle and provides a display indicative of the monitored impedance.

6 Claims, 7 Drawing Sheets

BRACHYTHERAPY NEEDLE WITH IMPEDANCE MEASUREMENT APPARATUS AND METHODS OF USE

FIELD OF THE INVENTION

The present invention relates to apparatus and methods for accurately depositing radioactive seeds into a patient's prostate in the vicinity of the patient's bladder.

BACKGROUND OF THE INVENTION

The American Cancer Society estimates that over 198,000 new cases of prostate cancer will be diagnosed in the United States in the year 2001 and nearly 31,500 men will die. Excluding non-melanoma skin cancers, prostate cancer is the most common cancer afflicting men in the United States.

Prostate cancer is defined as malignant tumor growth within the prostate gland. A staging system is a standardized way in which the extent to which a cancer is spread is described. The most commonly used system in the United States is called the TNM System of the American Joint Committee on Cancer. The TNM system describes the extent of the primary tumor (T), the absence or presence of metastasis to nearby lymph node (N), and the absence or presence of distant metastasis. (M).

There are four categories for describing the prostate cancer's T stage. In Stage T1, the tumor is not palpable but is detectable through prostate biopsy or prostatectomy specimen. In Stage T2, the cancer is palpable and is confined to the prostate. In Stage T3, the tumor extends locally beyond the prostate to the connective tissue next to the prostate and/or to the seminal vesicles, but does not involve any other organs. In Stage T4, the cancer has metastacized to the tissues next to the prostate such as the bladder's external sphincter, the rectum and/or the wall of the pelvis.

There are two N stages. Stage N0 indicates that the cancer has not spread to any lymph nodes. Stage N1 indicates the cancer has metastasized to one or more regional lymph nodes in the pelvis.

Finally, there are two M stages, M0 and M1. Stage M0 indicates that the cancer has not metastasized beyond the regional nodes. In comparison, Stage M1 means that metastases are present in distant (outside the pelvis) lymph nodes, in bones or other distant organs such as lungs, liver or brain.

In the early stages, prostate cancer is most commonly treated by either prostate removal or by brachytherapy. More advanced cases are treated by hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 2–5 days. Possible complications include impotence and urinary incontinence.

Internal radiation therapy or brachytherapy has recently been developed and holds great promise for the treatment of early stage prostate cancer. Radioactive pellets or seeds of, for example, iodine-125, palladium-103, or iridium-192, are deposited directly into the prostate through needle placement. U.S. Pat. No. 5,928,130 to Schmidt provides a slightly modified example of such a needle device.

Imaging techniques, such as transrectal ultrasound, CT scans, or MRI, are used to accurately guide placement of the radioactive material. Advantageously, radiation from the brachytherapy seeds is administered directly to the prostate with less damage to surrounding tissues, delivering a substantially higher radiation dosage to the prostate than to the surrounding tissues, as compared to external beam radiation therapy. The procedure need only be performed once, and impotence and urinary incontinence complications are significantly reduced, as compared to prostate removal procedures.

The seeds, which are permanently implanted, give off radiation for weeks or months. Their presence causes little discomfort, and they remain in the prostate after decay of the radioactivity. For several weeks following needle insertion, patients may experience pain in the perineal area, and urine may have a red-brown discoloration.

Although, when performed correctly, brachytherapy may provide several benefits when compared to prostate removal and other techniques, current apparatus and methods for delivering the seeds to target locations within the prostate are sub-optimal and are subject to practitioner error. Current methods of identifying the depth of needle insertion are ultrasound imaging or fluoroscopy. The junction of the base of the prostate and the bladder provides a common reference plane for needle insertion. Identifying this critical reference "base" plane is critical to proper needle and seed placement.

A previously known technique for imaging the base plane is to visualize the plane in either transverse or sagittal ultrasound imaging. Injection of contrast agent may facilitate imaging. A catheter, such as a standard Foley catheter, may be inserted into the patient's urethra proximal of the junction. Contrast agent comprising aerated K-Y jelly and water, may then be injected through an end port of the catheter. The agent moves distally towards the patient's bladder and is visible to an ultrasound probe, positioned in the patient's rectum, thereby facilitating imaging. However, bone structure and muscle may obstruct the image making accurate detection of tissue boundaries difficult. In the absence of reliable positional data, however, radioactive seeds may be inadvertently deposited into the patient's bladder rather than the distal region of the prostate.

Attempts have been made to improve Foley catheters, as well as to facilitate improved imaging within a body lumen. For example, U.S. Pat. No. 5,715,825 to Crowley provides an acoustic imaging catheter with an inflatable dilation balloon and an ultrasound transducer. However, while Crowley may provide improved imaging, the device is mechanically and electrically complex, and is therefore costly.

U.S. Pat. No. 5,916,153 to Rhea, Jr. provides a multifunction, modified Foley catheter. The device described in that patent, however, does not solve needle placement limitations present in previously known devices and methods.

In view of the drawbacks associated with previously-known methods and apparatus for radioactive seed placement, it would be desirable to provide methods and apparatus that accurately detect tissue boundaries.

It further would be desirable to provide methods and apparatus that provide reliable detection of the bladder/prostate tissue boundary.

It also would be desirable to provide methods and apparatus that may be used in conjunction with a standard brachytherapy apparatus.

SUMMARY OF THE INVENTION

In view of the foregoing, it is an object of the present invention to provide methods and apparatus that provide reliable detection of the prostate/bladder tissue boundary.

It is also an object of the present invention to provide methods and apparatus that may be used in conjunction with standard brachytherapy.

In accordance with the principles of the present invention, apparatus and methods are provided comprising an elongated needle and means for detecting the boundary between the prostate and the bladder. The needle includes two conductive traces each having a tip region at the distal end of the needle, and a lumen adapted to receive a column of radioactive seeds for deposition into the prostate once the distal end of the needle is properly positioned.

Impedance measurement circuitry coupled to the tip region of the conductive traces of the needle detects whether the distal end of the needle extends into the bladder or is disposed fully within the distal portion of the prostate. Once the distal end of the elongated needle penetrates into the mucosal lining of the bladder, the impedance of the tissue or fluid between the conductive traces decreases due to the change in tissue or the presence of fluid in the bladder. In particular, if the needle penetrates the mucosal lining into the bladder, the presence of electrolytes in urine within the bladder results in a rapid decrease in the measured impedance. Thus, the tissue boundary between the prostate and the bladder may be readily detected. The distal end of the needle then may be withdrawn back into the prostate for deposition of the radioactive seeds within the prostate. Thus, the present invention provides an improved method for detecting the tissue boundary between the prostate and the bladder for use in prostate brachytherapy treatment.

BRIEF DESCRIPTION OF THE DRAWINGS

Additional objects and advantages of the invention will be apparent from the following description, the appended claims, and the accompanying drawings, in which like reference characters refer to like parts throughout, and in which:

DETAILED DESCRIPTION OF THE PREFERRED EMBODIMENT

Figure 1:
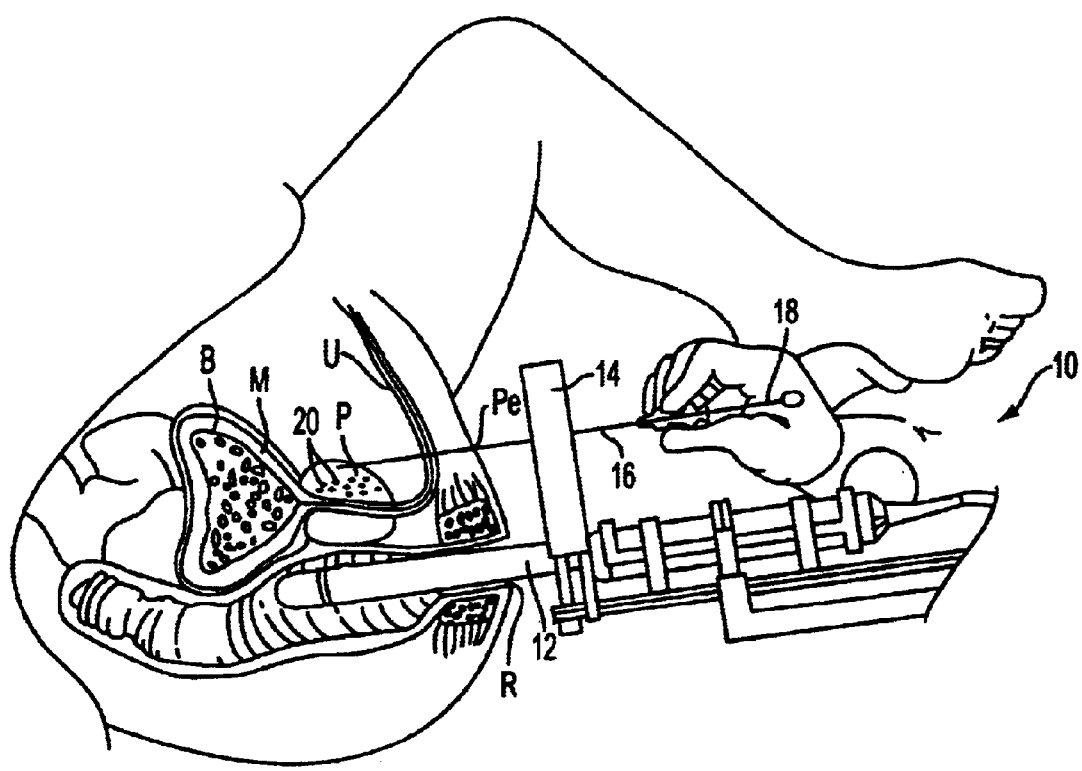
FIG. 1 is a schematic view of a prior art method of performing prostate brachytherapy.
Figure 2:
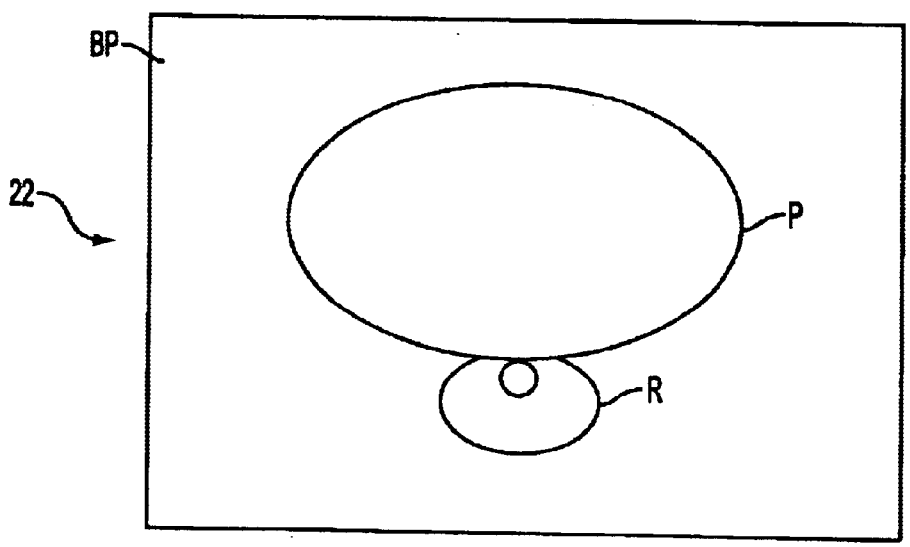
FIG. 2 is a schematic view detailing the prior art method of imaging the prostate/bladder tissue boundary in greater detail.

Referring now to FIGS. 1 and 2, a prior art method of performing brachytherapy for prostate cancer is described. The method and apparatus are as taught by Peter Grimm, DO, in a pamphlet entitled, "Ultrasound Guided Implantation of the Prostate: A Practical Review Course." As seen in FIG. 1, brachytherapy apparatus 10 comprises transrectal ultrasound probe 12, guide block 14, needle 16, plunger 18, and radioactive seeds 20. Ultrasound probe 12 is advanced through a patient's rectum R to facilitate imaging of the patient's prostate P. Prostate P surrounds urethra U and is just proximal of bladder B. The bladder is surrounded by a mucosal lining M. An ultrasonic image of a junction between the prostate and the bladder is acquired, as described below with respect to FIG. 2. Needle 16, loaded with seeds 20 and plunger 18, is then advanced through guide block 14, through the patient's perineum Pe, and into prostate P, where needle 16 is retracted while plunger 18 is held stationary to sew the seeds in a line within prostate P.

With reference to FIG. 2, the imaging aspect of the apparatus and method of FIG. 1 is described in greater detail. A catheter, such as a standard Foley catheter, is inserted into the patient's urethra proximal of the patient's prostate/bladder junction. A combination of water and KY jelly is then injected through an end port of the catheter. The combination moves distally towards the patient's bladder and appears to ultrasound probe 12 as contrast agent. Ultrasound probe 12 then provides signals that are converted by a previously known ultrasound system to display ultrasonic image 22 of base plane BP, which is located tangent to the distal surface of prostate P, i.e. at the prostate/bladder junction. All positions within the prostate are determined relative to base plane BP during a prostate brachytherapy procedure.

Ultrasonic imaging and location determination of base plane BP may be unreliable due to irregular ultrasonic images dependent on a density of the water/KY jelly combination at a given location, as well as flow conditions within the bladder and urethra. Thus, there exists a need for reliable apparatus and methods for prostate/bladder boundary detection. While an elongated needle for a prostate cancer brachytherapy procedure is described, the apparatus and methods described herein for tissue boundary detection may be utilized to detect tissue boundaries in other areas of the body such as subclavian vessel detection.

Figure 3:
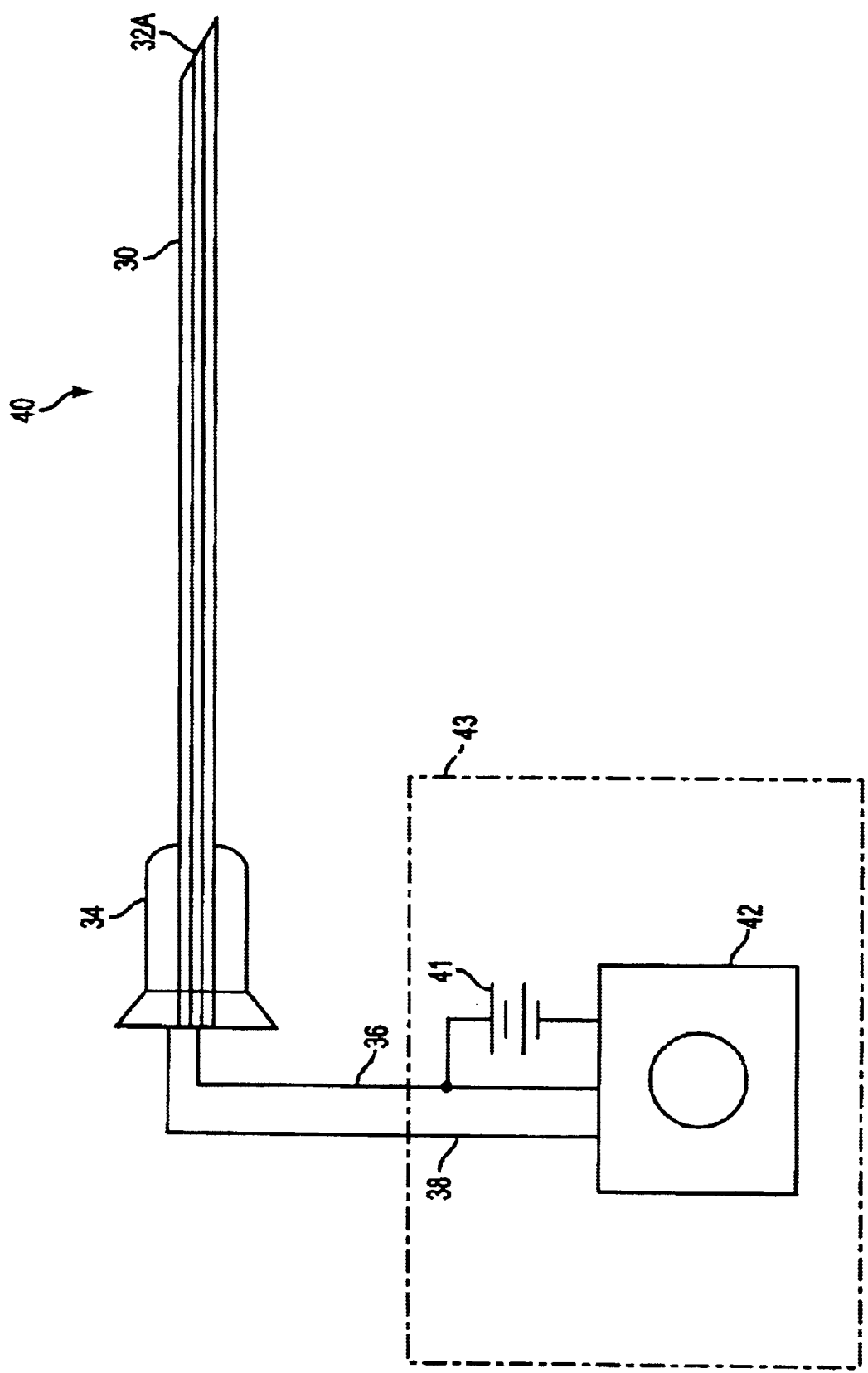
FIG. 3 is a side view, partly cut away, of an elongated needle of the present invention.

One embodiment of a needle constructed in accordance with the present invention is shown in FIG. 3. Brachytherapy needle device 40 of the present invention includes elongated needle 30, handle 34, wires 36 and 38, and circuitry 43. Circuitry 43 contains voltage source 41, and impedance measurement circuitry 42. Needle 30 contains conductive traces 32A and 32B (see FIG. 4B) along its outer circumference and includes a tip region at the distal end of the elongated needle 30.

Elongated needle 30 may be removably coupled to handle 34 which is used to position and guide needle 30. In an alternative embodiment, circuitry 43 may be contained within a reusable handle 34. Handle 34 may, for example, be formed from a polymer such as ABS, polystyrene, polyvinyl chloride, polysulfone or other suitable material.

Figure 4A:
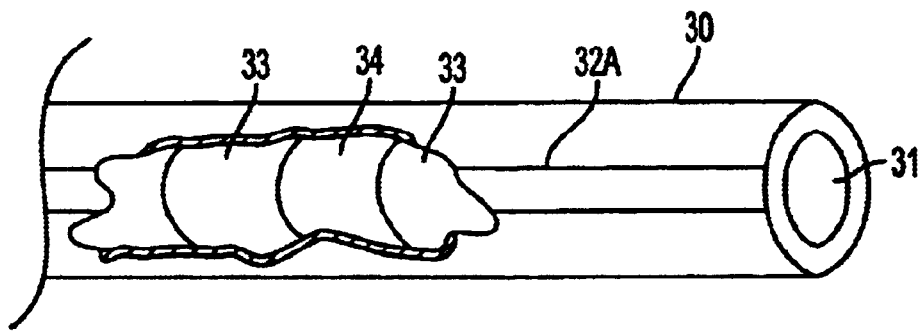
FIG. 4A is a depiction of a section of the elongated needle of the present invention.

Referring now to FIG. 4A, an expanded view of a portion of needle 30 is described. Needle 30 contains lumen 31 that extends from the proximal end to the distal end of the needle and is adapted to accept a column of radioactive seeds 33 and spacers 34. Preferably, a plunger 18 (see FIG. 1) is inserted through lumen 31 to deposit radioactive seeds 20 (see FIG. 1).

Figure 4B:
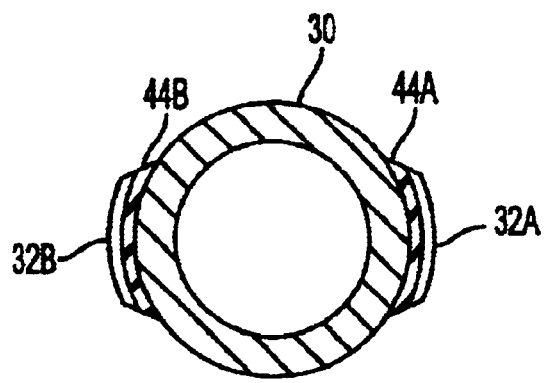
FIG. 4B is a cross section of the elongated needle of the present invention.

Referring to FIG. 4B, each of the conductive traces 32A and 32B extend from the proximal end to the distal end of elongated needle 30. Conductive traces 32A and 32B preferably are electrically insulated from each other and body tissue along the entire length of elongated needle 30. As shown in FIG. 4B, insulation strips 44A and 44B are disposed on the outer surface of needle 30 and insulate conductive traces 32A and 32B from the outer surface of needle 30. Conductive traces 32A and 32B are disposed on top of insulation strips 44A and 44B, respectively using techniques that are well-known in the art for forming thin film conductive traces, e.g. by gluing conductive foils, using thin-film deposition techniques, film etching, or laminating conductive foil between heat shrink tubing.

Elongated needle 30 may be made from a conductive material such as a metal or a metallic alloy and may be designed for either single-use or reuse. Insulating strips 44A and 44B may be made from an insulating material such as a nylon or polytetrafluoroethylene (PTFE) material. Conductive traces 32A and 32B may be formed from a metal or a metallic alloy. Suitable materials for conductive traces 32A and 32B include, for example, copper, nickel, or a composite of teflon and silver.

Referring again to FIG. 3, conductive trace 32A is electrically coupled to wire 36, and conductive trace 32B is electrically coupled to wire 38. Wires 36 and 38 are coupled to circuitry 43. Voltage source 41 is applied between wires 36 and 38. Impedance measurement circuit 42 continuously measures the impedance between wires 36 and 38. The impedance between wires 36 and 38 indicates how much current is flowing from wire 36 to wire 38. Because wires 36 and 38 are electrically insulated from each other and the tissue except in the tip region, current flows between conductive traces 32A and 32B only at the tip region at the distal end of needle 30.

Figure 5A:
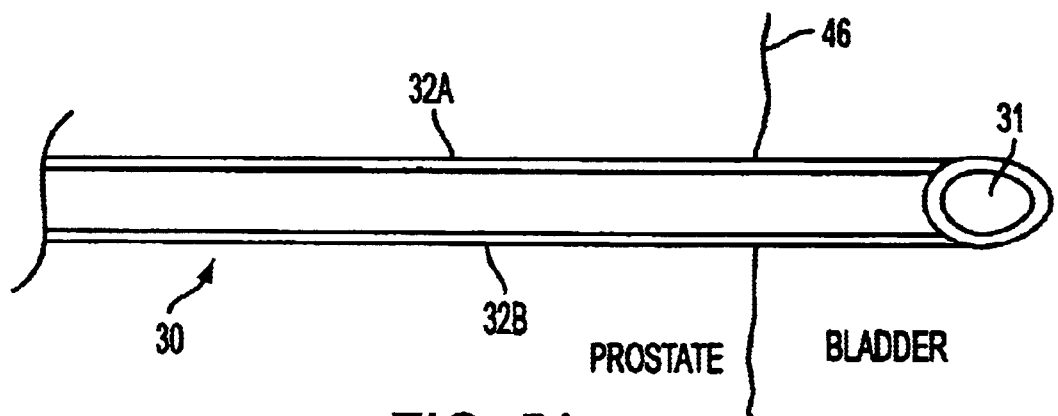
FIG. 5A is a depiction of an elongated needle of the present invention with the distal end of the elongated needle projected through the prostate/bladder tissue boundary into the bladder.

This impedance measuring of the present invention assists a clinician's detection of when the distal end of elongated needle 30 projects into the patient's bladder. When elongated needle 30 is inserted into the prostate, only a small amount of current flows between conductive traces 32A and 32B through tissue in the prostate, which has a relatively high impedance. The impedance measurement circuit 42 continuously measures a high impedance value while the distal end of elongated needle 30 is advanced through the prostate. When the distal end of elongated needle 30 projects into the bladder through the tissue boundary 46 (see FIG. 5A), the current flowing between traces 32A and 32B increases due to the presence of electrolytes in urine within the bladder.

Figure 5B:
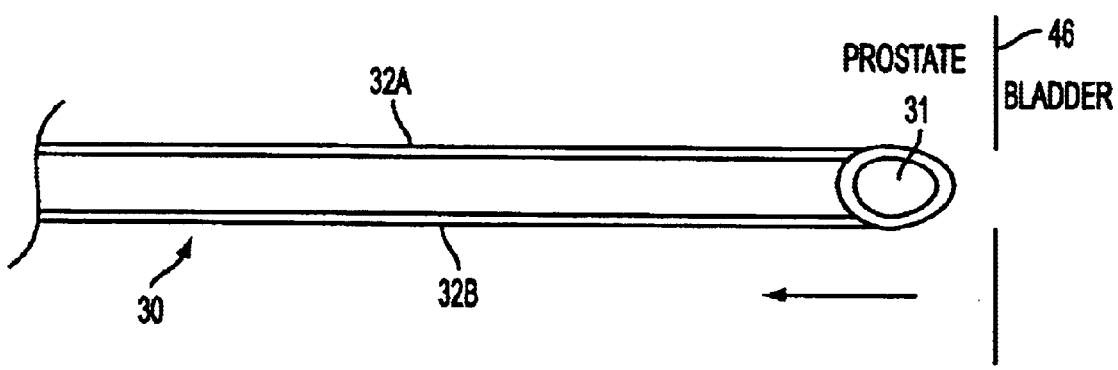
FIG. 5B is a depiction of an elongated needle of the present invention after it has been withdrawn back into the prostate from the bladder.

More current flows between wires 36 and 38 when the distal tip of needle 30 extends into the bladder than when the tip is fully disposed in the prostate. Impedance measurement circuitry 42 therefore measures a lower impedance between wires 36 and 38 when the tip regions of conductive traces 32A and 32B of elongated needle 30 project into the bladder. The reduction in impedance between wires 36 and 38 measured by the impedance measurement circuitry 42 indicates to the clinician that the tip region of the elongated needle 30 has penetrated the bladder/prostate boundary 46. The clinician then may withdraw needle 30 proximally as shown in FIG. 5B so that the tip region of elongated needle 30 is again fully within the prostate tissue. Elongated needle 30 then is operated to deposit a column of radioactive seeds and spacers within the prostate using a plunger inserted through lumen 31.

Figure 6:
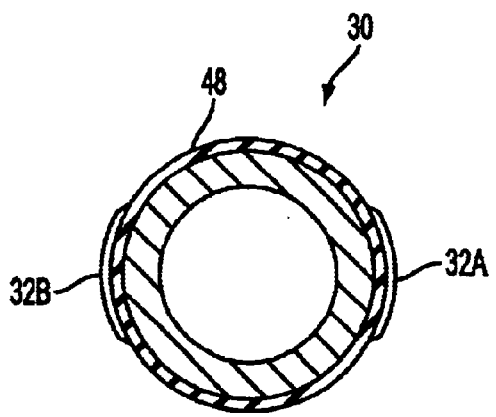
FIG. 6 is a cross section of an embodiment of the elongated needle of the present invention.

Referring now to FIG. 6, an alternative embodiment of needle 30 of the present invention is described. The outer surface of elongated needle 30 may be coated with non-conductive insulating material 48 that covers the entire outer surface of needle 30 around its circumference. Conductive traces 32A and 32B are disposed on the surface of insulation coating 48 using well known techniques as described for the preceding embodiment.

Figure 7A:
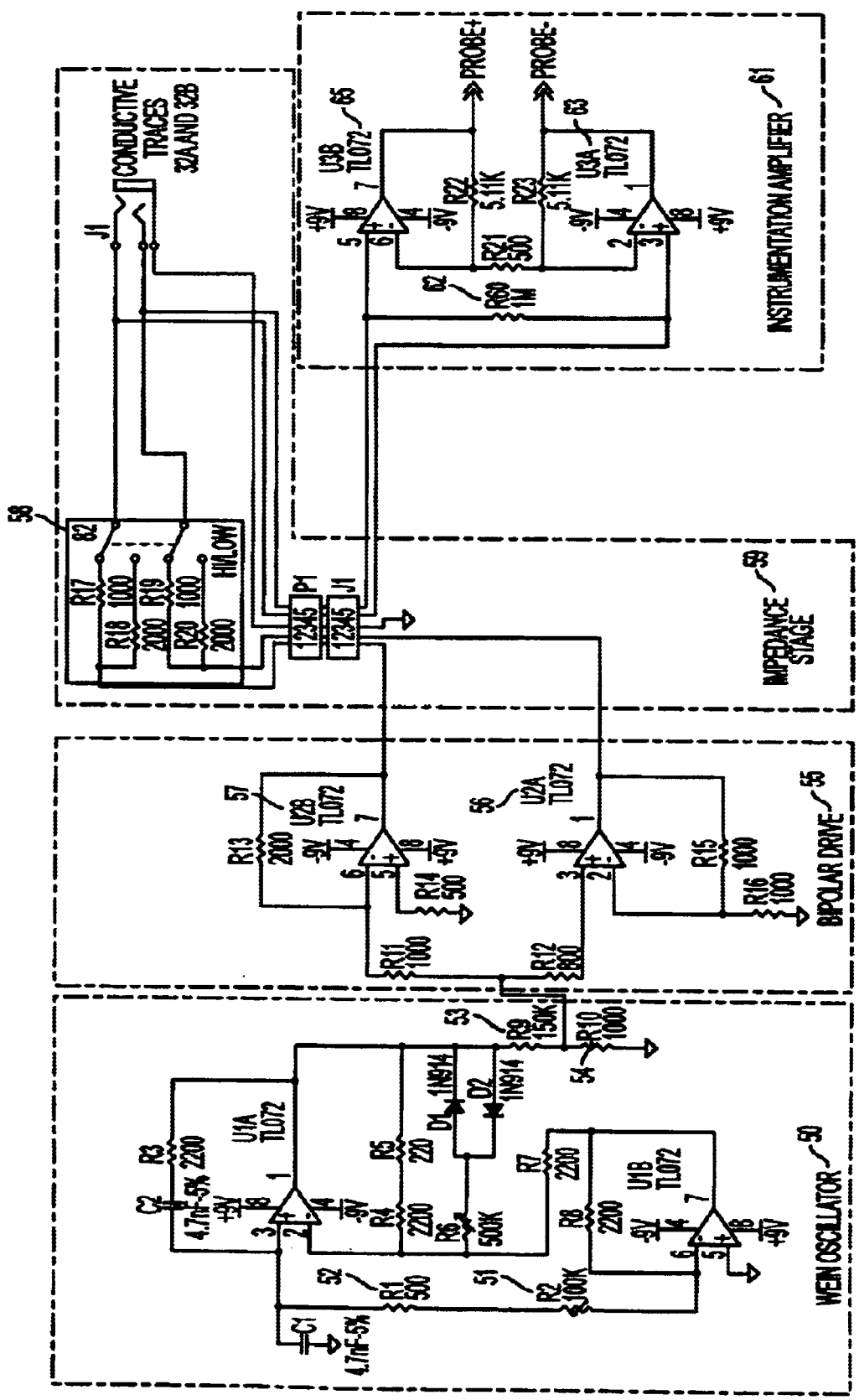
FIGS. 7A, 7B and 7C are schematic depictions of portions of an illustrative tissue boundary detection circuit of the present invention.
Figure 7B:
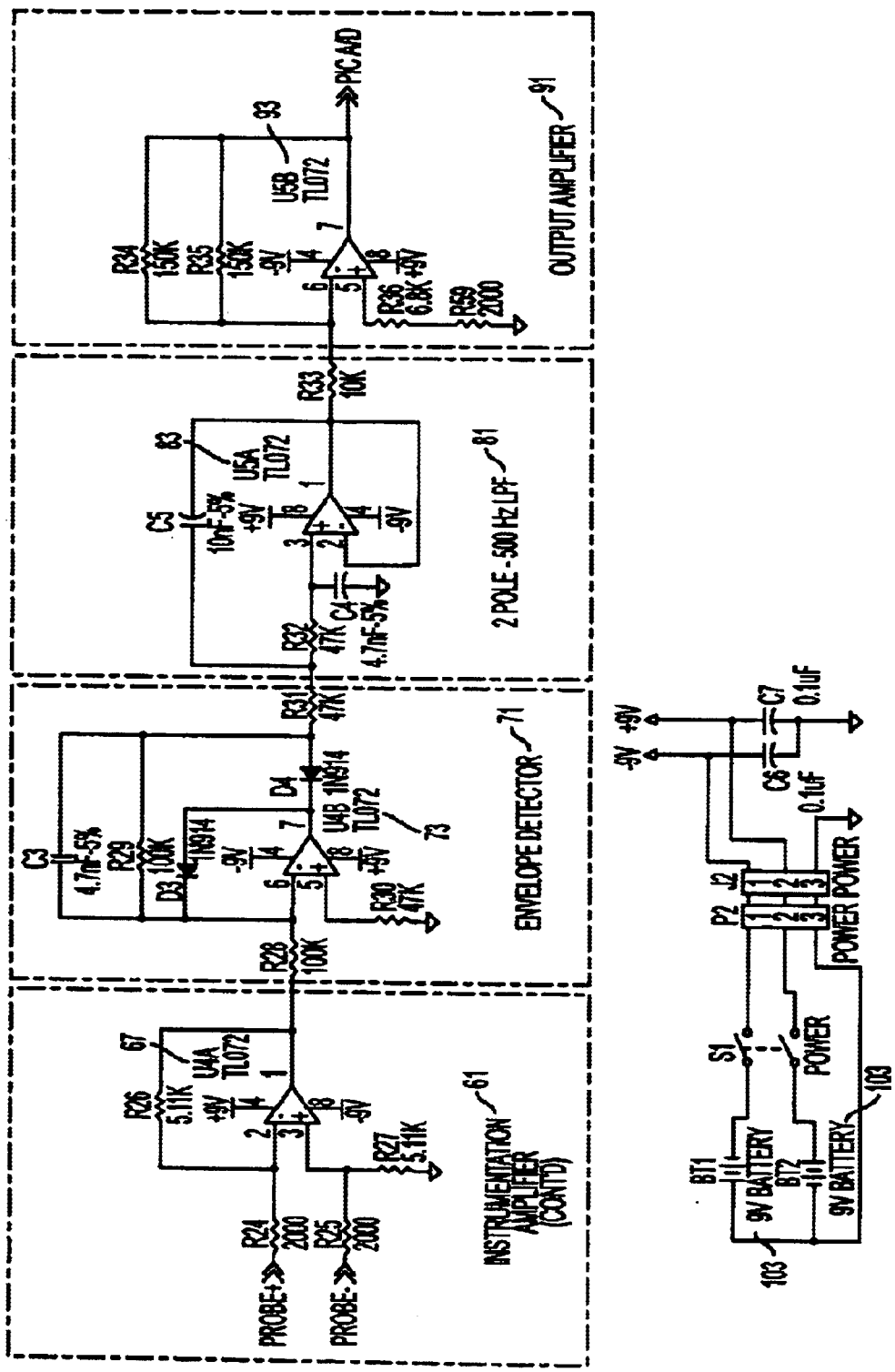
Figure 7C:
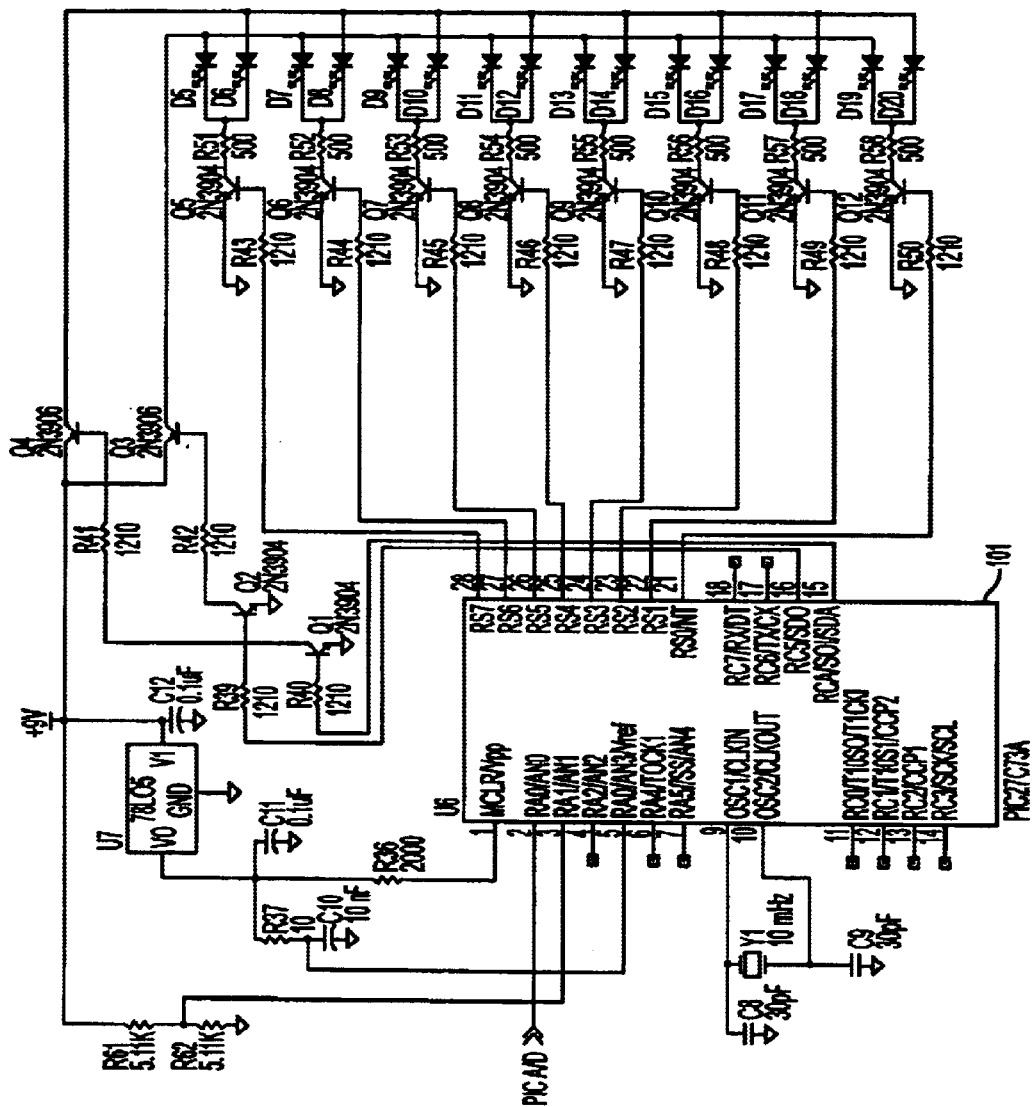

Referring now to FIGS. 7A–7C an illustrative embodiment of the impedance measurement circuitry is described. The analog portion of the tissue boundary detection circuitry begins with a Wein Oscillator 50 that generates two sinusoidal signals with a frequency between approximately 1 kHz and 30 kHz. The sinusoidal signals are 180° out of phase to acquire a balanced signal to the conductive traces 32A and 32B of needle 30. The frequency is controlled by variable trimmer (R2) 51. The output level is controlled by variable trimmer (R1) 52.

The output level of the Wein Oscillator is adjusted by voltage divider (R9) 53 and (R10) 54. The reduced voltage is applied to Bipolar Drive 55, implemented in (U2A) 56, (U2B) 57 and associated components. (U2A) 56 is a non-inverting amplifier with an approximate gain of 2. (U2B) 57 is an inverting amplifier, also with an approximate gain of 2. Each drive signal is approximately 50 mV peak-to-peak for a total drive of approximately 100 mV peak-to-peak applied to conductive traces 32A and 32B of needle 30.

The bipolar drive signal is applied to conductive traces 32A and 32B through resistor network 58 in the Impedance Stage 59. Resistor network 58 controls the impedance measurement range of conductive traces 32A and 32B. A high impedance measurement range is determined by resistors (R18) and (R20) and a low impedance measurement range is determined by (R17) and (R19). The resistance values may be adjusted to reflect the characteristics of the targeted tissue and the surrounding mucosa or tissue.

Referring still to FIGS. 7A and 7B, the output of Impedance Stage 59 is applied to Instrumentation Amplifier 61, implemented in (U3A) 63, (U3B) 65, (U4A) 67 and their associated components. The input impedance to Instrumentation Amplifier 61 is normally very high. In this illustration, the input impedance is limited to approximately 1 Mohm by resistor (R60) 62. If the impedance at the tip region of the conductive traces 32A and 32B of the elongated needle 30 is infinite, the full voltage from Bipolar Drive 55, approximately 100 mV is applied to the input of Instrumentation Amplifier 61. As the impedance at the tip region of conductive traces 32A and 32B of needle 30 approaches zero, the voltage applied to the input of Instrumentation Amplifier 61 also approaches zero.

In FIG. 7B, the output from Instrumentation Amplifier 61 is applied to Envelope Detector 71, implemented in (U4B) 73 and its associated components. Envelope Detector 71 removes the high frequency sinusoidal signal and generates a low frequency signal having an amplitude that is a function of the input carrier amplitude. The low frequency output signal from Envelope Detector 71 varies as a function of the impedance of the tissue or mucosa through which the tip region of conductive traces 32A and 32B of the elongated needle 30 passes.

The output of Envelope Detector 71 is negative going and also contains high frequency components of the carrier, which have not been completely filtered. To remove the remaining high frequency components, the signal is passed through 2-pole 500 Hz low pass filter 81, implemented in (U5A) 83 and its associated components.

The final analog stage, Output Amplifier 91, is implemented by (U5B) 93 and associated components. This stage inverts the filtered signal and amplifies it to approximately 4.8 volts when the impedance at the tip region of conductive traces 32A and 32B of needle 30 is infinite. This signal is applied to one of the microprocessor analog to digital inputs.

Referring to FIG. 7C, the remaining processing is done digitally in microprocessor (U6) 101. The microprocessor may be for example, a MicroChip Technologies PIC16C73A microprocessor or other suitable microprocessor. The microprocessor processes the input signal and continuously monitors the impedance measured to determine when the distal end of the elongated needle penetrates a tissue boundary. Microprocessor 101 preferably causes an indicator to display a metric corresponding to a sensed value of the tissue impedance.

In an alternative embodiment, the indicator may be a light meter that illuminates in response to the measured impedance as schematically depicted by the array of light emitting diodes in FIG. 7C. The tissue impedance measurement circuit is designed for battery operation and may be powered by two 9-volt cells 103 (see FIG. 7B). Because the power requirement for LEDs is quite high and may adversely affect battery life, a single illuminated LED at the extreme left of the light meter may indicate a maximum resistance at the distal end of elongated needle 30. As the probe is inserted into the prostate, a portion of the light bar will illuminate. As long as the needle is progressing through relatively homogeneous material, the length of the illuminated section of the bar will remain relatively constant. As the needle passes through a tissue boundary, the illuminated length of the light bar will grow or shrink, depending on the impedance characteristics of the new tissue or mucosa. As the impedance sensed at the distal end of elongated needle 30 approaches zero, all LEDs in the light meter may be illuminated.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure and are intended to fall within the scope of the appended claims.

What is claimed is:

1. A method for depositing radioactive seeds into a patient's prostate in the vicinity of the patient's bladder, the method comprising:

providing a device comprising a needle having proximal and distal ends, and a lumen extending therebetween and adapted to accept a column of radioactive seeds and spacers, and means for detecting whether the distal end of the needle projects into the patient's bladder;

inserting the needle through the patient's prostate until the means for detecting indicates that the distal end is disposed in the bladder;

withdrawing the needle proximally until the means for detecting indicates that the distal end is no longer disposed in the bladder; and operating the needle to deposit the column of radioactive seeds and spacers into the patient's prostate.

2. The method of claim 1 wherein the device further comprises a single-use needle and a reusable handle, the method further comprising removably coupling the needle to the handle.

3. The method of claim 1 wherein the means for detecting comprises circuitry for measuring tissue impedance, the method further comprising continuously measuring tissue impedance during the steps of inserting the needle and withdrawing the needle.

4. The method of claim 3 wherein the means for detecting comprises a light meter, the method further comprising illuminating the light meter responsive to the measured impedance.

5. The method of claim 1 wherein the device further comprises a plunger disposed within the lumen in contact with a proximal end of the column of radioactive seeds and spacers, and operating the needle comprises maintaining the plunger stationary while retracting the needle proximally.

6. A method for treating prostate cancer comprising:

providing a needle having a lumen, proximal and distal ends, first and second conductive traces, and means for detecting a tissue boundary coupled to the first and second conductive traces;

inserting the needle into a patient's prostate;

measuring an impedance of tissue disposed between the first and second conductive traces using the means for detecting a tissue boundary;

monitoring the impedance measured by the means for detecting a tissue boundary to determine when the distal end penetrates a boundary between the patient's prostate and an adjacent mucosa of the patient; and withdrawing the needle from the mucosa so that the distal end is disposed fully within the patient's prostate.

* * * * *